United States Patent
Chiang et al.

(10) Patent No.: US 6,221,059 B1
(45) Date of Patent: Apr. 24, 2001

(54) FLOW-DIRECTED CATHETER SYSTEM AND METHOD OF USE

(75) Inventors: Andrew Chiang, Fremont; Mark E. Deem, San Francisco, both of CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/295,209

(22) Filed: Apr. 21, 1999

Related U.S. Application Data

(62) Division of application No. 08/667,011, filed on Jun. 21, 1996, now Pat. No. 5,899,890.

(51) Int. Cl.$^7$ .................................................. A61M 5/00
(52) U.S. Cl. ........................................ 604/264; 604/523
(58) Field of Search .................................. 604/508, 525, 604/528, 529, 264, 265, 266, 267, 268, 271, 523, 524, 526, 527, 530

(56) References Cited

U.S. PATENT DOCUMENTS

| | | |
|---|---|---|
| 3,995,623 | 12/1976 | Blake et al. . |
| 4,024,871 | 5/1977 | Stephenson . |
| 4,469,483 | 9/1984 | Becker et al. . |
| 4,500,676 | 2/1985 | Balazs et al. . |
| 4,739,768 | 4/1988 | Engelson . |
| 4,838,879 | 6/1989 | Tanabe et al. . |
| 5,171,232 | 12/1992 | Castillo et al. . |
| 5,203,777 | * 4/1993 | Lee ........................................ 604/529 |
| 5,256,158 | 10/1993 | Tolkoff et al. . |
| 5,336,205 | 8/1994 | Zenzen et al. . |
| 5,453,099 | 9/1995 | Lee et al. . |
| 5,489,277 | * 2/1996 | Tolkoff et al. ........................ 604/529 |
| 5,496,292 | 3/1996 | Burnham . |
| 5,542,937 | 8/1996 | Chee et al. . |
| 5,662,622 | * 9/1997 | Gore et al. ............................ 604/526 |
| 5,695,457 | * 12/1997 | St. Goar et al. ...................... 604/523 |
| 5,891,112 | * 4/1999 | Samson ................................ 604/523 |
| 5,944,712 | * 8/1999 | Frassica et al. ...................... 604/523 |
| 6,042,876 | * 3/2000 | Deem ................................... 427/2.28 |

FOREIGN PATENT DOCUMENTS

| | | |
|---|---|---|
| WO 92/19308 | 11/1992 | (WO) . |
| WO 93/23105 | 11/1993 | (WO) . |
| WO 96/01662 | 1/1996 | (WO) . |

\* cited by examiner

*Primary Examiner*—Manuel Mendez

(57) ABSTRACT

A flow-directed catheter comprises a catheter body having a relatively rigid proximal body segment and a relatively flexible, supple distal body segment. The distal body segment may have a reduced diameter relative to the proximal body segment, at least at its distal tip. Radiopaque markers are provided at the transition between the two body segments and at the tip of the catheter. The radiopaque markers are preferably recessed entirely within the catheter body. Optionally, the distal body segment may have surface irregularities which enhance the ability of the distal body segment to follow blood flow. A flow-directed catheter system comprises the catheter in combination with a coaxial sheath to selectively strengthen at least the proximal of the distal body segment. The catheter may be used for a variety of diagnostic and/or therapeutic procedures.

14 Claims, 10 Drawing Sheets

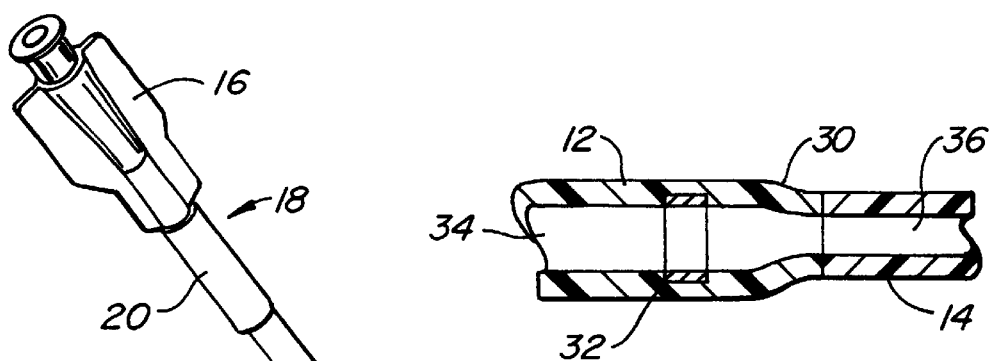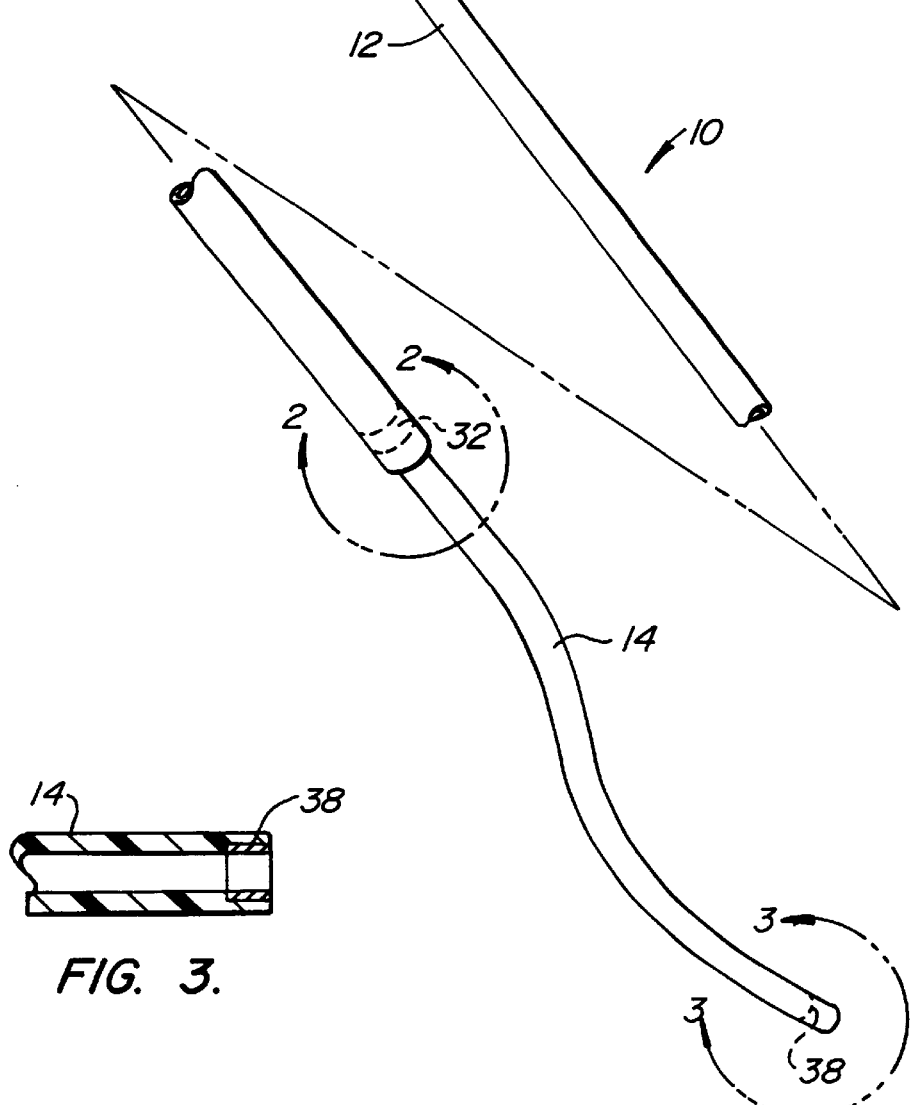

FLOW-DIRECTED CATHETER SYSTEM AND METHOD OF USE

This application division of, and claims the benefit of priority from application no. 08/667,011, filed on Jun. 21, 1996 now U.S. Pat. No. 5,899,890, the full disclosure of which is incorporated herein by reference.

BACKGROUND OF THE INVENTION

1. Field of the Invention

The present invention relates generally to the field of intravascular catheters. More particularly, the present invention relates to an apparatus, system, and method for the flow-directed introduction of catheters to a patient's vasculature.

Flow-directed catheters are designed so that the flow of blood through an artery directs the catheter tip along the arterial flow path and to the target site. One type of flow-directed catheter uses an enlarged balloon or cup-shaped end to create a partial obstruction causing the blood flow to pull the tip of the catheter in the direction of the blood flow. See, for example, U.S. Pat. Nos. 3,995,623 to Blake et al. and 4,024,873 to Antoshkiw et al.

Another type of flow-directed catheter has a very flexible distal end which is designed to be carried along by the blood flow instead of by partially blocking the artery. One of this type is manufactured by Balt S.A. of France under the trademark MAGIC. It is made of a hydrophobic material with a relatively stiff proximal section, a moderately flexible midsection and a quite flexible distal section. While this catheter has enjoyed some success, it has several shortcomings. The inside diameter of the distal section is quite small and is often not usable with a guidewire. If a guidewire is used the guidewire tends to pull on and stretch the distal section and damage the floppy tip. A guidewire could also puncture the wall of the distal section. The MAGIC catheter also includes a region of intermediate stiffness between the relatively stiff proximal section and the very flexible distal end. While facilitating a catheter introduction, such a transition section requires an additional bond within the catheter body to accommodate the additional section. The additional bond, in turn can create a constriction on the inside of the catheter lumen which can obstruct the relatively weak distal section of the catheter and can block the catheter during infusion of various agents. Blockage can cause rupture of the catheter, placing the patient at risk.

Another prior art flow-directed catheter is manufactured by Target Therapeutics of Fremont, Calif. and is sold under the trademark Zephyr. It is intended to be used with a mandrel which allows the stiffness of the entire catheter to be increased during introduction through a guide catheter. The mandrel is removed before the catheter is advanced into the vasculature. The Zephyr has a lubricous, hydrophilic coating on its outside surface to aid passage of the catheter through the guiding catheters and vessels. A problem with this catheter is that it suffers from the similar limitations of the Magic catheter due to its small diameter. Also, this catheter is too stiff to access distant vascular structures. See U.S. Pat. No. 5,336,205.

Heretofore, flow-directed catheter designs have had to compromise between flexibility, which is required for the distal portion to follow blood flow, and column strength, which is required to advance the catheter from its proximal end. In order to properly balance such contrary objectives, catheters having multiple zones of flexibility have been proposed. For example, U.S. Pat. No. 5,336,205, describes a catheter having a proximal zone which is relatively rigid, an intermediate zone having an intermediate flexibility, and a distal zone which is highly flexible and capable of following blood flow. While a workable compromise, the length of the distal zone is sometimes too short for a desired treatment protocol. While catheters having flexible regions of different lengths could be provided, the need to maintain an inventory of multiple catheters is undesirable. Additionally, even if an inventory of catheters having transition zones of different lengths were available, it is often not possible to predict which length would be most effective for treating any individual patient or condition. Thus, after starting a procedure, it would often be necessary for a physician to exchange catheters having transition zones of different lengths if the initially chosen catheter is unable to access the treatment site. The need to exchange catheters increases the cost, duration, and risk of patient complication.

A second problem faced by many flow-directed catheters is the need to occasionally rely on a guidewire to guide the catheter past branches in the vasculature. Because of the small dimensions of prior flow-directed catheters and the high surface friction of the materials normally used in the flexible distal sections of such catheters, it has been very difficult to employ conventional guidewires to assist in catheter placement. Moreover, the additional constrictions resulting from the bond(s) required to accommodate the intermediate transition section(s) create another potential impediment to guidewire advancement. Thus, for use with flow-directory catheters, guidewires should have a highly lubricous surface, be very radiopaque (to permit visualization), should have shapeable distal sections, and should also have soft, atraumatic tips. No one guidewire currently available meets all of these requirements adequately.

For these reasons, it would be desirable to provide flow-directed catheters, flow-directed catheter systems, and methods for introducing flow-directed catheters which overcome at least some of the shortcomings discussed above. In particular, it would be desirable to provide flow-directed catheters where the stiffness of the most flexible regions of the catheter could be varied while advancing the catheter through the vasculature. It would be further desirable to provide catheter systems and methods for introducing such catheters which facilitate use of guidewires for occasionally advancing the flow-directed catheters through portions of the vasculature. Such catheter and guidewire systems should allow the catheter to be introduced by flow, by pushing (with the catheter selectively stiffened with an internal guidewire), or by guiding over the guidewire.

2. Description of the Background Art

U.S. Pat. Nos. 5,336,205; 4,024,873; and 3,995,623, have been discussed above. Another flow-directed catheter design is shown in copending application Ser. No. 08/399,677, assigned to the assignee of the present invention. Microcatheter designs having regions of varying flexibility are described in U.S. Pat. No. 4,739,768 and copending application Ser. No. 08/534,089, assigned to the assignee of the present application. Catheters having radiopaque fillers in their bodies are described in U.S. Pat. Nos. 5,171,232 and 4,469,483. A flow-directed catheter having a lubricous coating is described in WO 96/01662. Catheters having surface irregularities to reduce sliding friction with coaxial catheters are described in U.S. Pat. No. 5,496,292; WO 93/23105; and WO 92/19308.

SUMMARY OF THE INVENTION

According to the present invention, a flow-directed catheter comprises a catheter body including a proximal body segment having a proximal end, a distal end and a lumen therethrough, and a distal body segment having a proximal end, a distal end, and a lumen therethrough. The proximal end of the distal body segment is joined to the distal end of the proximal body segment, and the two body segments will have differing flexibilities, with the proximal body segment being relatively rigid and having sufficient column strength to facilitate axial positioning of the catheter in a guide catheter and the vasculature. In contrast, the distal body segment will be very flexible and supple so that it is able to follow blood flow when present in a blood vessel. Preferably, the catheter body will consist essentially of the proximal body segment and distal body segment without additional body segments having different flexibility or other characteristics.

In a first aspect of the present invention, the lumen and outer diameters of the distal body segment will be reduced relative to those of the proximal body segment. Preferably, the distal body segment will have uniform lumen and outer diameters along its entire length. The proximal body segment will also have uniform lumen and outer diameters along its length. The internal and external diameters of the proximal section will usually be larger than those of the distal section. Usually, the distal end of the proximal section will be "necked down" to accommodate the change in internal diameter from the proximal section to the distal section. In this way, the inner diameter (and optionally the outer diameter) of the relatively stiff proximal section will be equal to that of the distal section of the catheter at the point where the two sections are bonded together. This is advantageous since the point where the diameter is decreased will be a region of stress concentration subject to kinking and collapse. By locating that region in the stiffer, stronger proximal section, any tendency for the catheter to kink or collapse will be reduced. Moreover, if such a collapse does occur, any blockage of fluids will be confined to the stronger proximal section, thus reducing the chance that the catheter will fail. Exemplary lumen and outer diameters for the distal body segment will be in the range from 0.1 mm to 1.25 mm and 0.33 mm (1F) to 1.67 mm (5F), respectively. Exemplary inner and outer diameters for the proximal body segment will be in the range from 0.1 mm to 1.25 mm and 0.33 mm (1F) to 2 mm (6F), respectively.

In a second aspect of the present invention, the flow-directed catheter will comprise a radiopaque marker located near the junction region between the proximal body segment and the distal body segment. Usually the radiopaque marker will be a metal band which is recessed in the distal end of the proximal body segment, typically having an inner surface which is generally flush with the lumen of the catheter.

In a third specific aspect of the present invention, at least a portion of the outer surface of the distal body segment will comprise surface irregularities which increase flow resistance between the outer surface and blood flow past the outer surface. Such enhanced flow resistance will improve the ability of the distal body segment to follow blood flow. The surface irregularities will usually be disposed at least near the distal end of the distal body segment usually being disposed over substantially the entire outer surface of the distal body segment. Exemplary surface irregularities include ridges, bumps, cavities, fibers, and the like.

In a fourth aspect of the present invention, at least the distal body segment will have a hydrophilic coating to facilitate introduction and positioning of the flow-directed catheter, both with and without use of a guidewire. optionally, the entire catheter body would be coated with a hydrophilic material, such as hyaluronic acid covalently bonded onto the surface of the catheter by heat curing. It has been found that such hydrophilic coatings also facilitate removal of the distal ends of the catheters, particularly when they have become embedded within a blood vessel lumen, e.g., after release of an adhesion or other occlusive agent from the catheter. Hyaluronic acid (HA) coatings are particularly preferred since HA is a biologically compatible material. Most previous hydrophilic coatings have been petrochemically based.

The present invention further provides flow-directed catheter systems including a flow-directed catheter as described above in combination with a sheath which is coaxially received over the flow-directed catheter. The sheath has a proximal end, a distal end, and a lumen therethrough which is slidably disposed over the catheter. The sheath may be axially positioned to selectively enhance the flexibility and column strength of a proximal portion of the distal body segment. Such selective enhancement of column strength facilitates positioning of the catheter through tortuous regions of the vasculature, as described in more detail below in connection with the methods of the present invention. The sheath may be generally uniform along its length or may have variable stiffeners, tapering, or other characteristics to further control the properties of the catheter.

The present invention still further provides catheters including recessed radiopaque markers disposed at their distal ends. Such catheters include a catheter body having a proximal end, a distal end, and a lumen therethrough. The distal end has an inner cylindrical surface, an outer cylindrical surface, and an annular end surface. The radiopaque marker is disposed near the distal end of the catheter and recessed entirely within the envelope defined by the inner and outer cylindrical surfaces and the annular end surface. Usually, the catheter body is composed of an organic polymer and the radiopaque marker is composed of a metal band coil, metal fragments, or the like. In a preferred embodiment, the radiopaque marker band is recessed entirely within an annular channel formed in the inner cylindrical surface, where the end of the radiopaque marker band is flush with the annular end surface of the catheter body. Alternatively, the marker may be formed by doping a circumferential segment of the catheter body with a radiopaque agent, such as barium, sulfate, bismuth trioxide, or the like.

According to the method of the present invention, a catheter is provided having a proximal body segment, a distal body segment, and a lumen therethrough. Flexibility of the distal body segment is substantially greater than that of the proximal body segment to permit introduction of the catheter in a flow-directed manner. A distal end of the catheter is advanced from a guide catheter into a target blood vessel, whereby the blood flow can carry the distal end of the body segment in the direction of blood flow. A stiffening element is repositioned over or within the distal body segment of the catheter, whereby flexibility of the distal body segment within the blood vessel may be selectively varied to facilitate positioning of the catheter. In a first aspect of the method, the stiffening element is a guidewire which may be selectively positioned within a central lumen of the catheter. optionally, the guidewire may be advanced from the distal end of the catheter and used to guide the catheter through the vasculature by selectively positioning through branches in the vasculature. Usually, after passing a specific branch in the vasculature, the guidewire will be retracted back into the catheter so that the distal body segment is again subject to the blood flow as the catheter -is advanced. Alternatively, the stiffening element may be a sheath which is coaxially received over the catheter, as generally described above in connection with the catheter system of the present invention.

BRIEF DESCRIPTION OF THE DRAWINGS

FIG. 1 is a perspective view of a flow-directed catheter constructed in accordance with the principles of the present invention.

FIG. 2 is a detailed view taken in region 2—2 of FIG. 1.

FIG. 3 is a detailed view taken in region 3—3 of FIG. 1.

DESCRIPTION OF THE SPECIFIC EMBODIMENTS

Figure 3A:
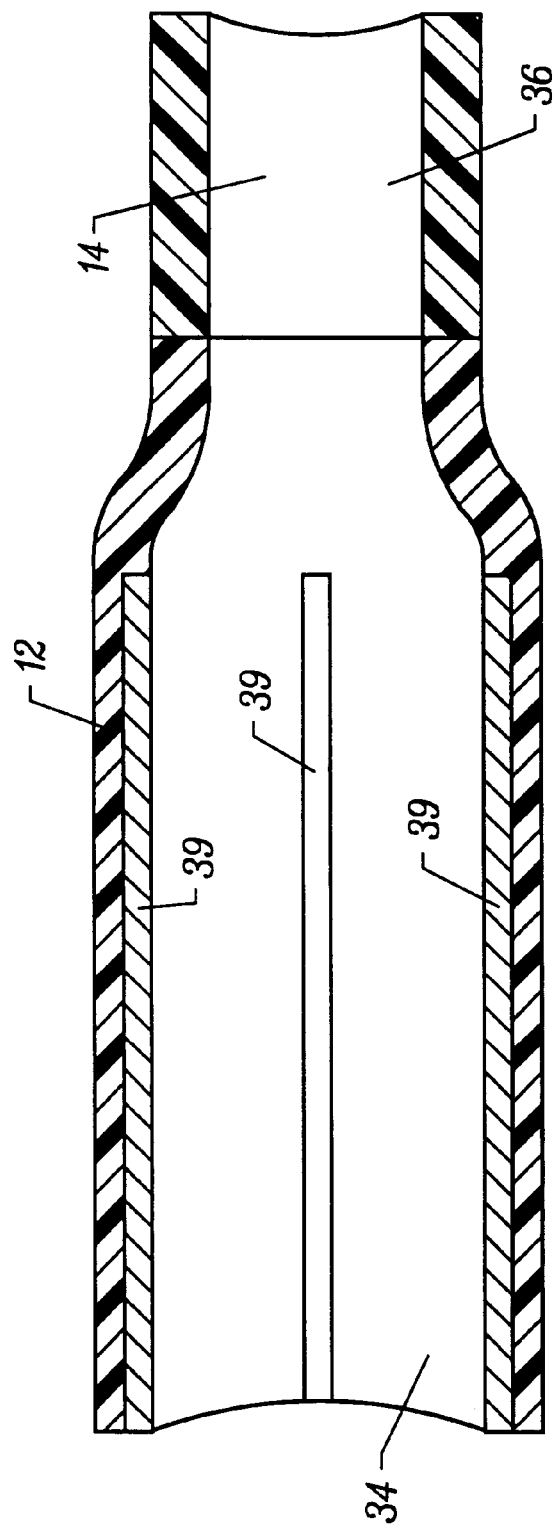
FIG. 3A is a cross-sectional view of a catheter of claim 1 having a longitudinal strip pattern radiopaque marker.

Flow-directed catheters according to the present invention will comprise a catheter body having a proximal body segment, a distal body segment, and a continuous lumen extending through both body segments. The proximal and distal body segments will have different physical and dimensional characteristics which permit the catheter to be introduced to patient's vasculature in a flow-directed protocol, i.e. where the distal body segment is carried through branching blood vessels by the blood flow through said vessels. Except as described hereinafter, the direction and guiding of the distal body segment of the catheter will not require use of a guidewire for selecting between branching vessels. A guidewire or optional coaxial sheath may be used, however, for selectively reinforcing or stiffening a portion of the distal body segment in order to control flexibility and enhance positioning of the catheter in the vasculature.

The flow-directed catheter will have a total length in the range from 60 cm to 250 cm, usually from 135 cm. to 175 cm. The length of the proximal segment will typically be from 20 cm to 220 cm, more typically from 100 cm to 120 cm. The length of the distal body segment will typically be in the range from 5 cm to 85 cm, usually from 35 cm to 55 cm. The proximal and distal body segments will preferably be joined directly to each other, i.e. without any intermediate zones therebetween. The body segments may be joined in any conventional manner, such as heat fusion, adhesive bonding, coextrusion, or the like. In the exemplary embodiment, the two body segments will be formed separately thereafter fused together by the application of heat.

The catheters of the present invention may be composed of any biologically compatible polymeric resins having suitable characteristics when formed into the tubular catheter body segments. Exemplary materials include polyvinyl chloride, polyethers, polyamides, polyethylenes, polyurethanes, copolymers thereof, and the like. The distal segment may be formed from more elastic materials, such as latex rubber, silicone rubber, and blends thereof. Preferably, both the proximal Body segment and distal body segment will be composed of a polyvinyl chloride (PVC), with the proximal body segment being formed from a relatively rigid PVC and the distal body segment being formed from a relatively flexible, supple PVC. Optionally, the proximal body segment may be reinforced with a metal or polymeric braid or other conventional reinforcing layer.

The proximal body segment will be sufficiently rigid to permit axial positioning of the catheter through a guide catheter with the distal body segment extending into the patient's vasculature. The proximal body segment will typically have a shore hardness in the range from 50D to 100D, preferably being about 70D to 80D. Usually, the proximal shaft will have a flexural modulus from 20,000 psi to 1,000,000 psi, preferably from 100,000 psi to 600,000 psi. The distal body segment will be sufficiently flexible and supple so that it may be carried by blood flow through the patient's vasculature. Typically, the shore hardness of the distal body segment will be in the range from 20A to 100A, preferably being from 55A to 80A. The flexural modulus for the distal segment will be from 50 psi to 15,000 psi, preferably from 100 psi to 2000 psi.

The catheter body may further comprise other components, such as radiopaque fillers; colorants; reinforcing materials; reinforcement layers, such as braids and helical reinforcement elements; or the like. In particular, it would be possible to reinforce the proximal body segment in order to enhance its column strength while optionally limiting its wall thickness and outside diameter. Usually, however, it will not be necessary to enforce the proximal body segment. Moreover, it will generally be undesirable to reinforce the flexible body segment in any way which significantly reduces its flexibility.

The diameter of the distal body segment will usually be smaller or tapered down from that of the proximal body segment. Usually, the proximal body segment will have a constant diameter, within an outer diameter in the range from 0.33 mm to 2 mm, usually from 0.67 mm to 1.67 mm, and an inner diameter in the range from 0.1 mm to 1.25 mm, usually from 0.2 mm to 1 mm. The distal body segment usually also have a constant diameter, with an outer diameter in the range from 0.33 mm to 1.67 mm, usually from 0.67 mm to 1.33 mm, and an inner lumen diameter in the range from 0.1 mm to 1.25 mm, usually 0.2 mm to 1 mm. Alternatively, the distal body segment can be tapered, where its proximal end has a diameter which generally is the same as that of the distal end of the proximal body segment and its distal end has a diameter in the range set forth above for distal body segments having a constant diameter.

Usually, radiopaque markers will be provided at least at the distal end and the transition region between the proximal and distal body segments. Other radiopaque markers may be provided elsewhere. A preferred distal radiopaque marker comprises a metal band which is fully recessed within the distal tip of the distal body segment. Preferably, the radiopaque metal band will be recessed in an annular channel formed at the distal end of the lumen through the distal body segment. Similarly, the radiopaque marker at the transition between the distal and proximal body segments will also be recessed and aligned coaxially with the lumen in the catheter. The present invention further comprises catheters having such recessed radiopaque marker bands, particularly at their distal ends.

Referring now to FIGS. 1–3, and exemplary flow-directed catheter 10 constructed in accordance with the principles of the present invention comprises a catheter body including a proximal body segment 12 and a distal body segment 14. A standard luer connector 16 is attached to a proximal end 18 of the proximal body segment 12, and usually a strain relief sleeve 20 is provided. As best illustrated in FIG. 2, a shoulder 30 is provided near the distal end of the proximal body segment 12, and a radiopaque marker 32 is preferably provided near the shoulder, at the transition, usually being recessed within lumen 34 of the proximal body segment 12. The inner diameter of the radiopaque marker ring 32 is shown to be generally concentric with the lumen 34 in the proximal body segment 14, but it could also be concentric and aligned with the lumen 36 of the distal body segment.

A distal radiopaque marker ring 38 is recessed within the distal tip of distal body segment 14, as best seen in FIG. 3. Recessing of both the transition marker ring 32 and the distal marker ring 38 is particularly advantageous since it reduces the chance that the marker rings will be lost from the catheter. Recessing the marker rings 32 and 38 within the inner lumen of the catheter also facilitates guidewire movement through the lumen. In particular, by positioning the marker rings 32 and 38 flush with the lumenal wall, the possibility of the guidewire snagging on the marker ring(s) is greatly reduced. Additionally, any impediment to inflow of liquid reagents through the catheter lumen is significantly reduced. Thus, marker ring placement according to the present invention is advantageous in that the rings do not protrude into the inner catheter lumen or protrude outwardly from the catheter body or they can interfere with catheter placement. In particular, an exterior ring at the distal tip of the catheter may become inadvertently caught in a blood vessel being treated, particularly within an adhesive or other occlusive agent being at least from the distal tip of the catheter. FIG. 3A shows a catheter where at least a portion of the body segments includes a radiopaque filler, wherein the filler is disposed or concentrated in a pattern and the pattern comprises longitudinal stripes.

Figure 4:
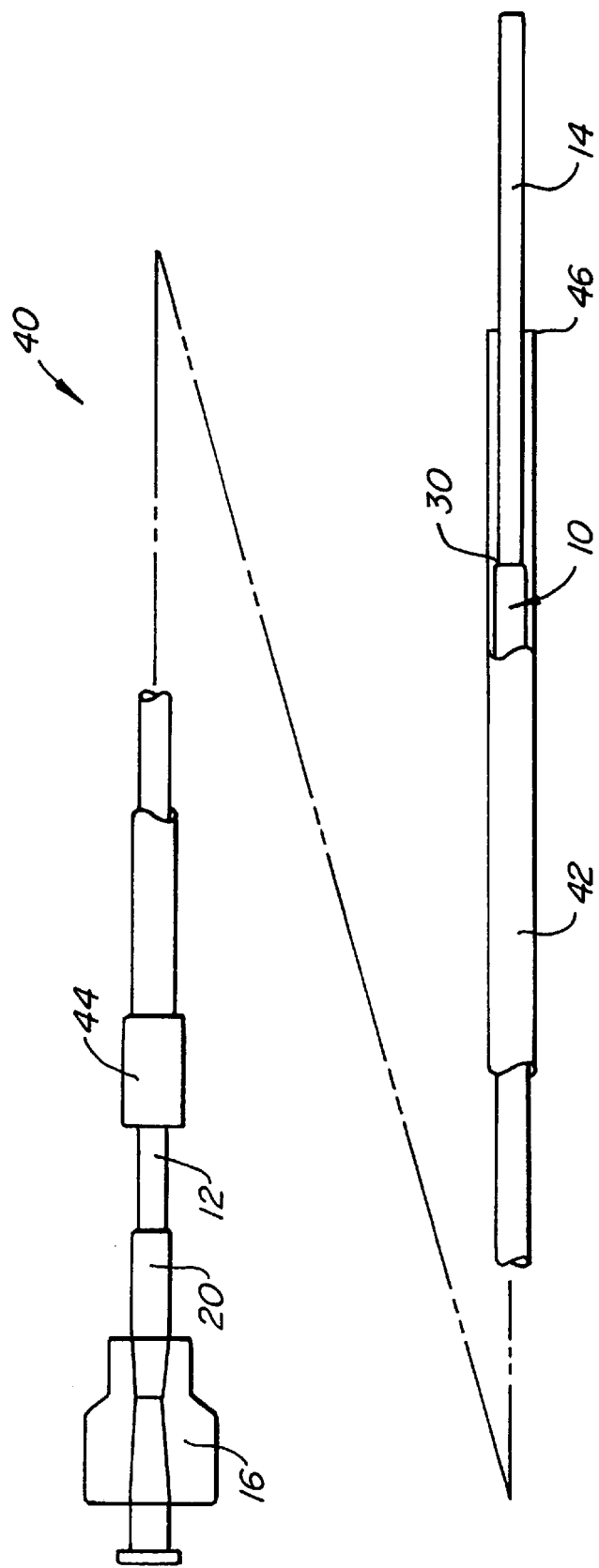
FIG. 4 illustrates a flow-directed catheter system constructed in accordance with the principles of the present invention comprising the flow-directed catheter of FIG. 1 in combination with a sheath-like stiffening member for selectively adjusting the flexibility of a distal body segment of a catheter.

Referring now to FIG. 4, a flow-directed catheter system 40 comprises the flow-directed catheter 10 of FIG. 1 in combination of an outer sheath or sleeve 42. The sheath 42 has a hub 44 at its proximal end and a distal end 46 which may be axially positioned over the distal body segment 14 of catheter 10. The hub 44 may frictionally engage the proximal body segment 12, or a locking means (not shown) may be provided to fix the relative axial position of the sheath and the catheter 10. By selectively positioning the distal end 46 of the sheath along the length of the distal body segment 14, the effective stiffness of a proximal portion of the distal body segment 14 may be adjusted. It will be appreciated that in some instances, the catheter 10 may be more readily positioned if at least a portion of the proximal region of the distal body segment 14 has a greater column strength. Such greater column strength can be-achieved by advancing the sheath 42 coaxially over the distal body segment 14 by a distance selected to provide a desired incremental amount of column strength. As discussed below, such selective stiffening of the distal body segment 14 may also be achieved by using a guidewire within the lumen of the distal body segment 14.

Figure 5:
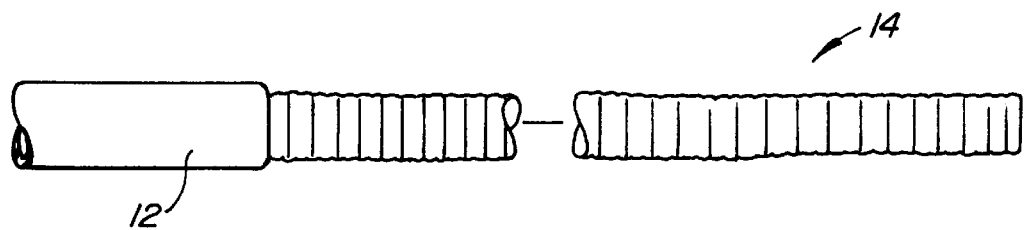
FIGS. 5–8 illustrate alternative constructions of the distal body segment of the flow-directed catheter of FIG. 1.
Figure 6:
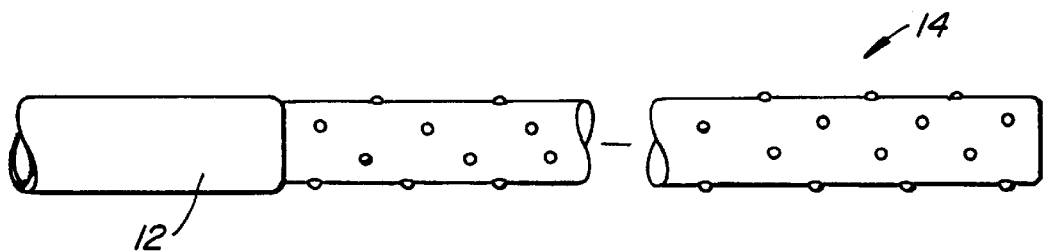
Figure 7:
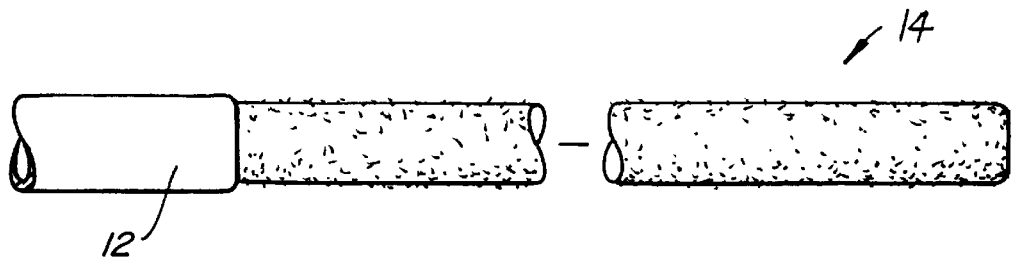

Referring now to FIGS. 5–8, the outer surface characteristics of the distal body segment 14 may be modified in a variety of ways to achieve different catheter characteristics. For example, the outer surface of distal body segment 14 may be modified to have ridges or corrugations, as shown in FIG. 5, surface bumps or protrusions, as shown in FIG. 6, or short fibers or hairs as shown in FIG. 7. Surface dimpling (not shown) would also be useful. Each of these embodiments would increase relative flow resistance between the distal body segment 14 and blood flow past the distal body segment. Such increased flow resistance would improve the ability of the distal segment to follow the blood flow through the vasculature.

Figure 8:
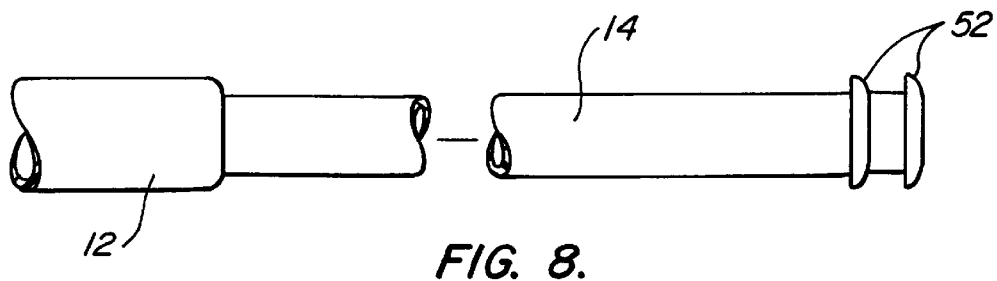
Figure 9:
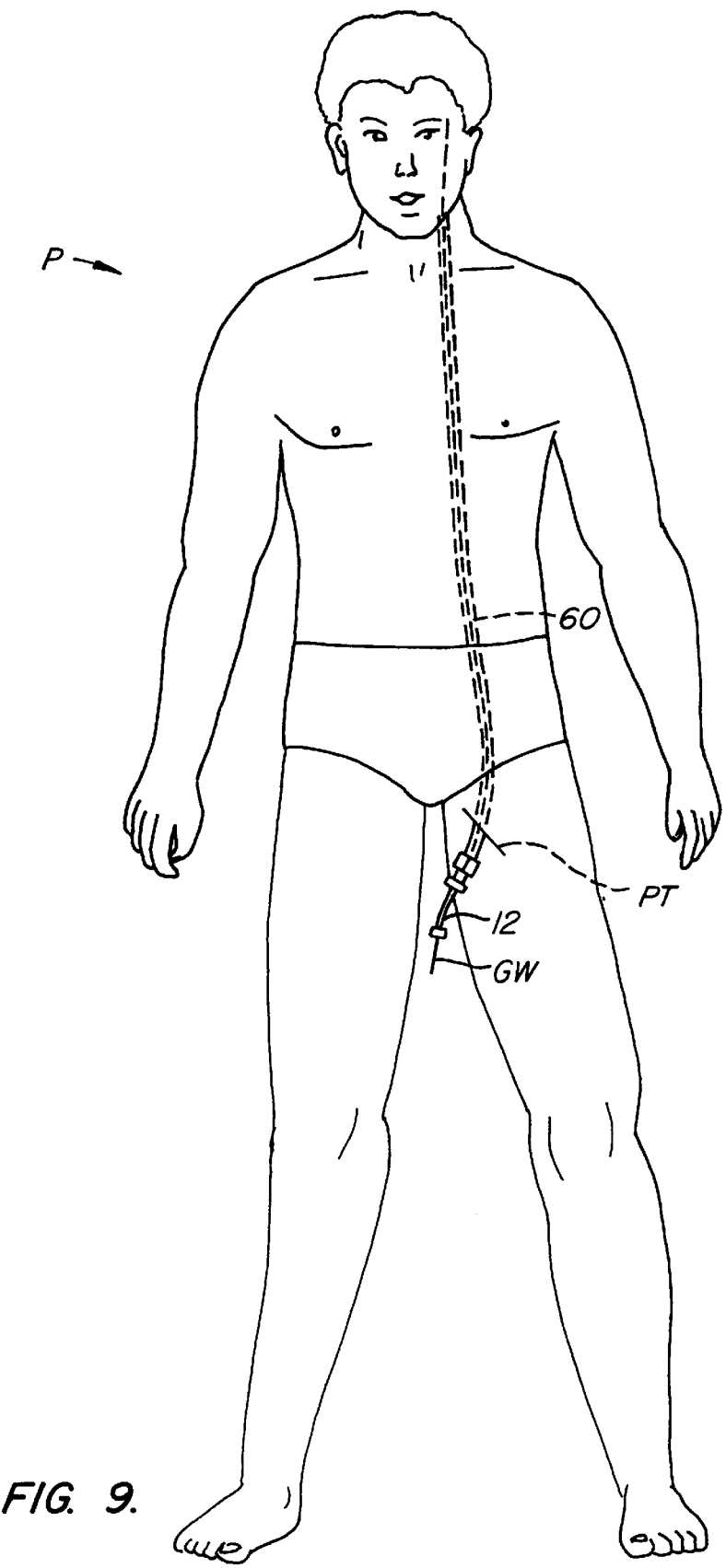
FIG. 9 illustrates a patient having a flow-directed catheter introduced to the cerebral vasculature using a guide catheter passing through the groin and femoral artery, according to the method of the present invention.
Figure 10:
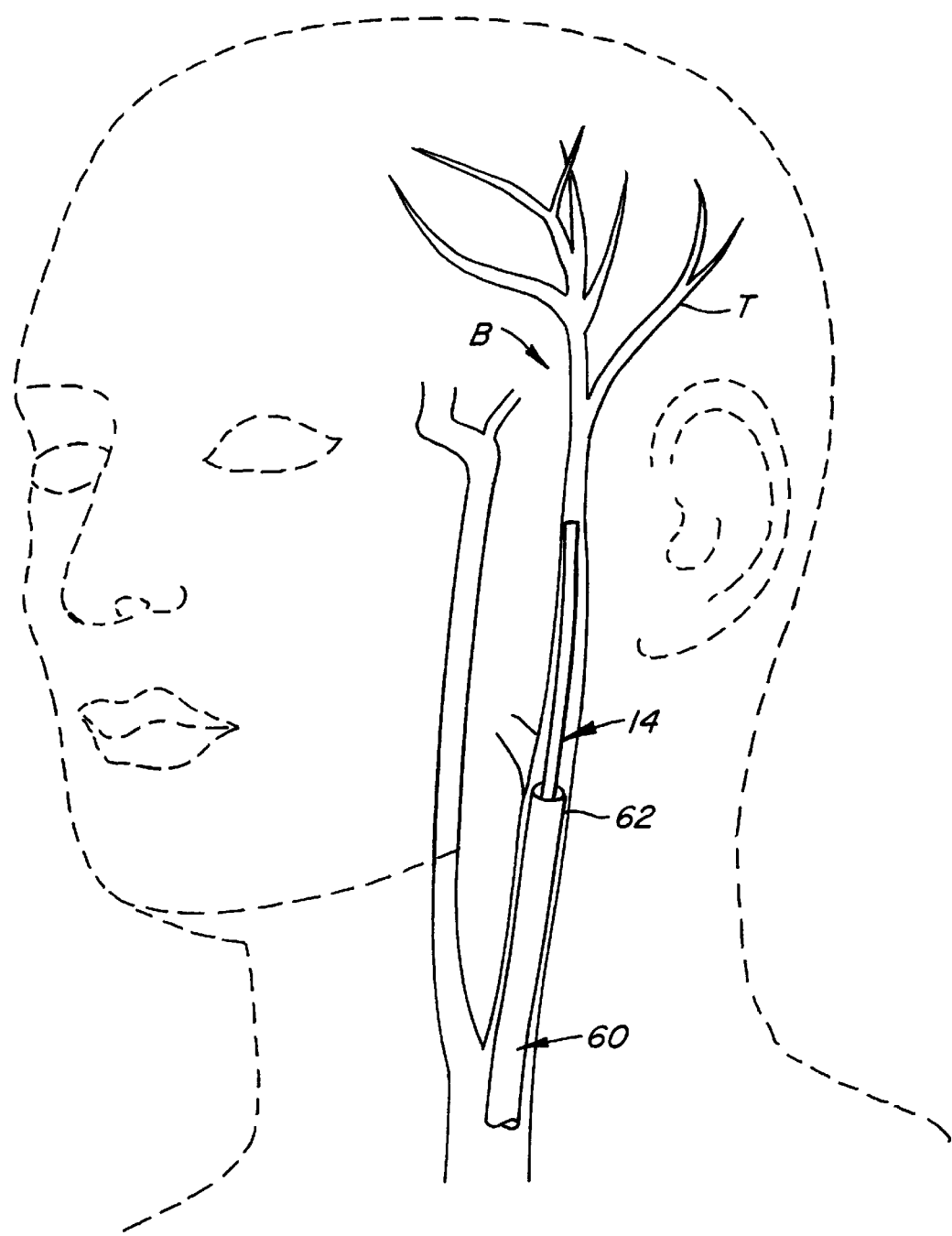
FIG. 10 is an enlarged view of the guide catheter and distal body segment of the flow-directed catheter at the point of entry into the cerebral vasculature.

As an alternative to modifying the surface characteristics along the entire length of the distal body segment, it is possible to provide flow-resistive elements just at the distal end of the distal body segment 14, as shown in FIG. 8, where a pair of spaced-apart flanges 52 is illustrated.

Optionally, the distal body segment 14 and/or proximal body segment 12 may be coated with a hydrophilic material, such as hyaluronic acid or a salt thereof. Additionally, the inner lumens 34 and 36 of the proximal and distal body segments 12 and 14 respectively, may also be coated with a hydrophilic material. Specific techniques for applying such coatings are described in U.S. Pat. Nos. 5,037,677; 5,023,114; 4,959,074; 4,801,475; 4,663,233; 4,487,865; and 4,500,676, the full disclosures of which are incorporated herein by reference.

Referring now to FIGS. 9–13, introduction of the flow-directed catheter 10 to the cerebral vasculature of a patient P is illustrated. A guide catheter 60 is introduced into the femoral artery through a penetration PT inn the patient's groin. The guide catheter is advanced from the femoral artery through the descending aorta, aortic arch, and common cardioid arteries until a distal tip 62 reaches a target artery at the base of the skull, as best observed in FIG. 12. The distal body segment 14 may then be advanced from the distal end 62 of the guide catheter 60 into the first artery. The objective of the treatment will be to advance the distal tip of the distal segment 14 into a target artery T which requires selectively directing the distal tip past a branch B in the arteries.

Figure 11:
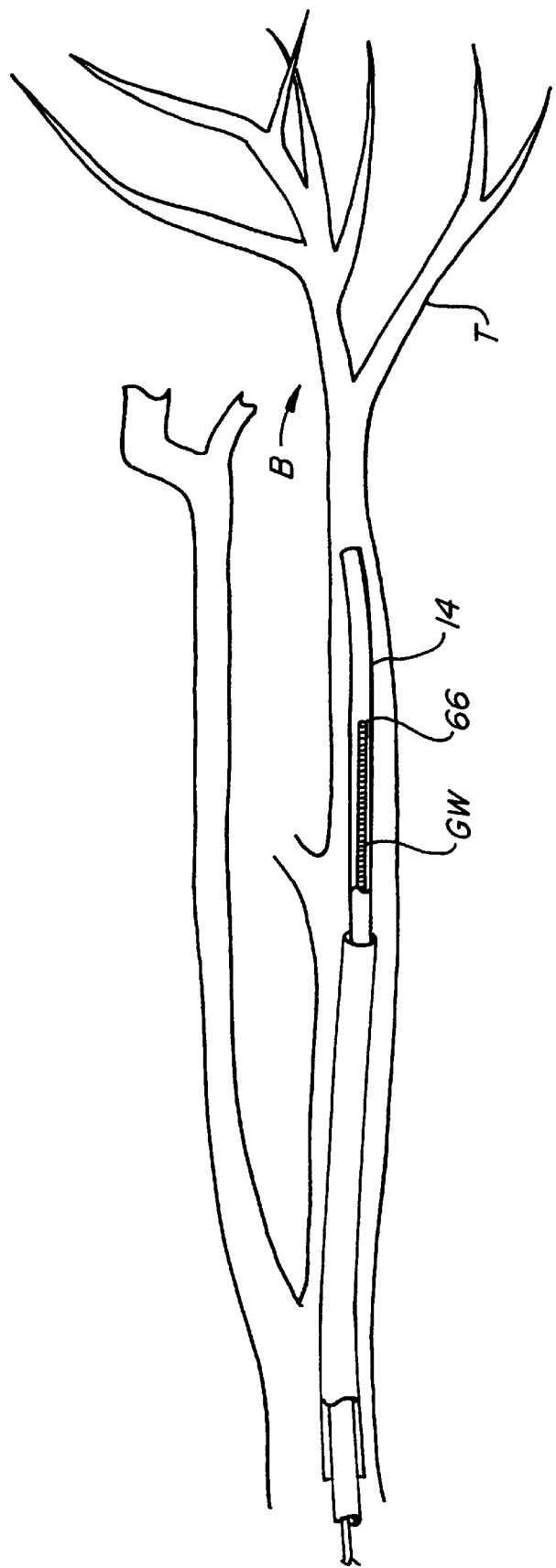
FIGS. 11–13 are detailed views of the method of positioning the flow-directed catheter of the present invention.

Initially the distal segment 14 may be advanced through the artery by manually advancing the proximal end 12 to permit the distal body segment 14 to be carried by blood flow toward the target artery T. Optionally, a guidewire GW may be positioned so that its distal end 66 is located within the distal body segment 14, as best illustrated in FIG. 11. Such positioning of the guidewire GW selectively reinforces the column strength of the distal body segment, which in turn enhances the ability to position the catheter 10.

Use of guidewire retracted within the distal body segment 14 can provide a "variable" transition section within the distal segment itself. That is, the physician can actually position the guidewire within the distal body segment 14 during a procedure to obtain greater or lesser stiffness within the distal segment as required. Such choice of stiffness is a significant advantage when the catheter is being positioned primarily by pushing on the proximal end. In this way, the need to exchange catheters in order to introduce additional catheter(s) having transition sections of different lengths is avoided. Preferred guidewires are disclosed in copending application Ser. No. 08/665,973 (attorney docket no. 16255-003500), the full disclosure of which is incorporated herein by reference.

The preferred guidewire will also be hydrophilically coated, preferably with hyaluronic acid or an equivalent biological polysaccharide. The guidewire will have a coil tip comprising a helically wound filament where adjacent turns of the coil are spaced apart by a distance equal to 15% to 50%, preferably 25% to 35%, of the width of the filament. The filament typically has a circular cross-section with a diameter in the range from about 0.02 mm to 0.1 mm, and the spacing between adjacent turns will usually be from about 0.01 mm to 0.05 mm. Such coils may be coated with the preferred hyaluronic acid layer without significant loss of flexibility or bendability. The hyaluronic coating is also particularly compatible with flow-directed catheter having their lumens coated with hyaluronic acid. Thus, the present invention further comprises systems and kits comprising the flow-directed catheters in combination with the guidewire. Such kits will further comprise packaging, such as a pouch or box. The packaging will preferably be sterile and will usually include instructions for use setting forth the methods described elsewhere herein.

Figure 12:
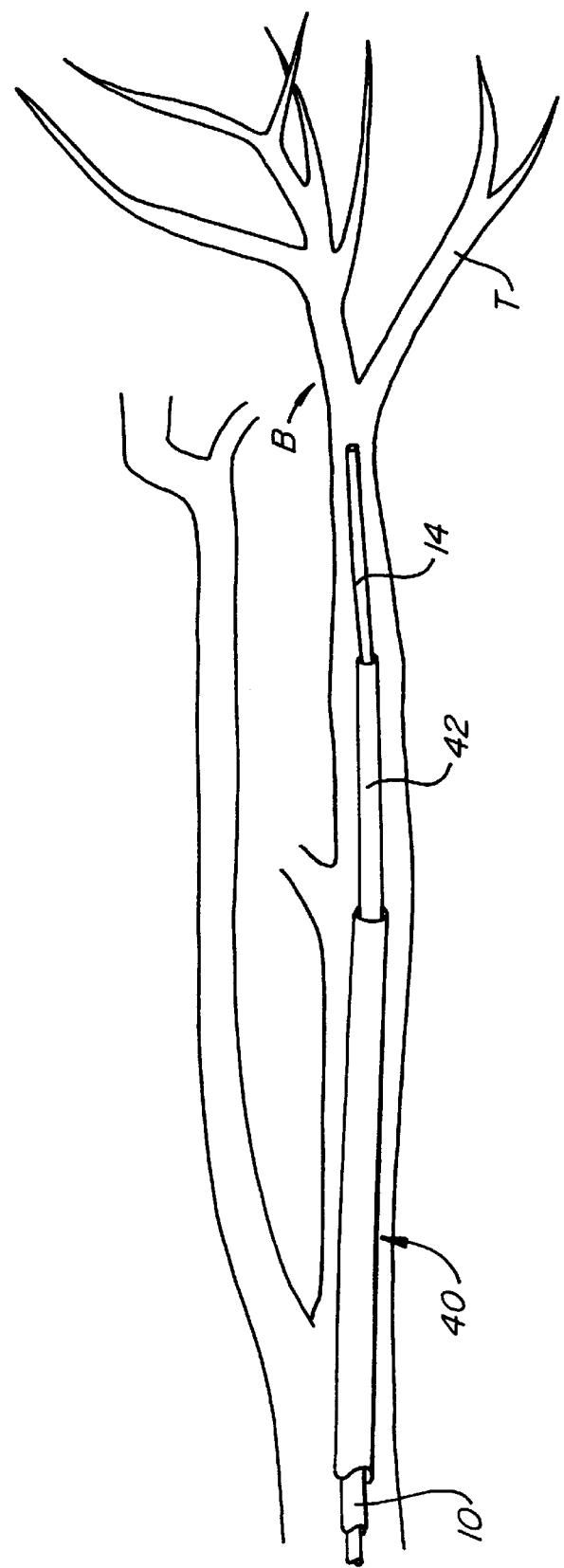
Figure 13:
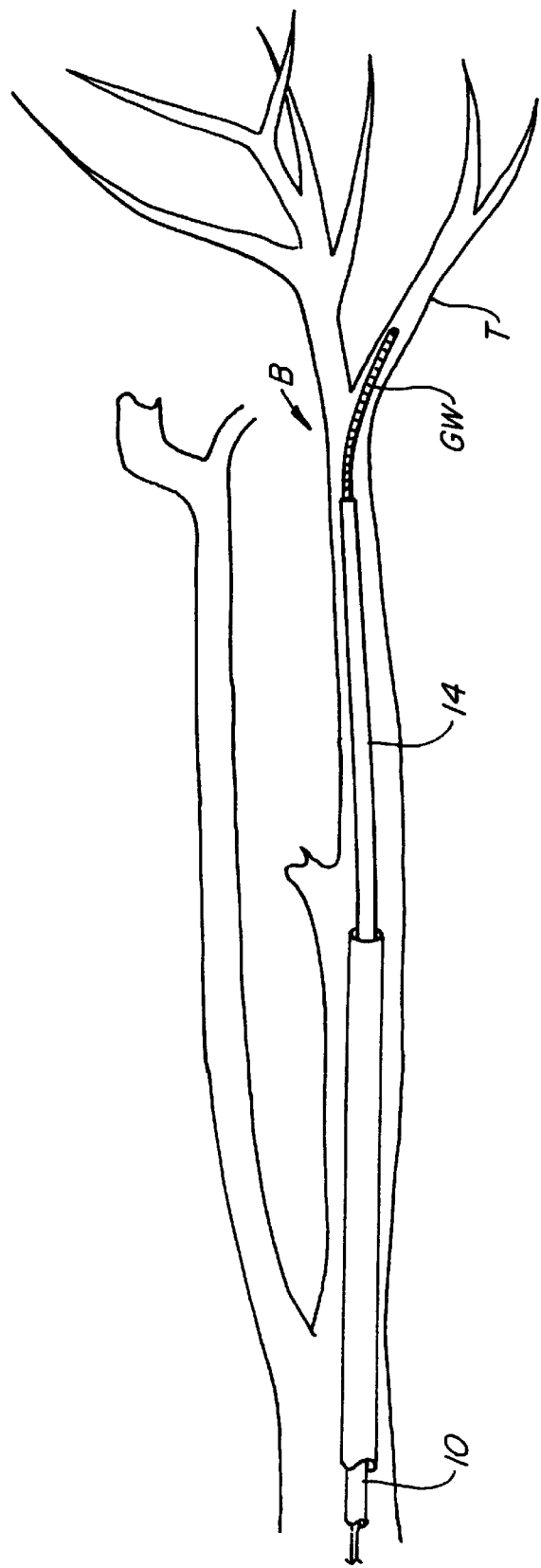

As an alternative to use of the guidewire GW the catheter system 40 may be employed, and the sheath 42 selectively positioned over the distal body segment 14 as illustrated in FIG. 12. Use of the sheath 42 will also selectively enhance the column strength of the proximal region of distal body segment 14.

Figure 15:
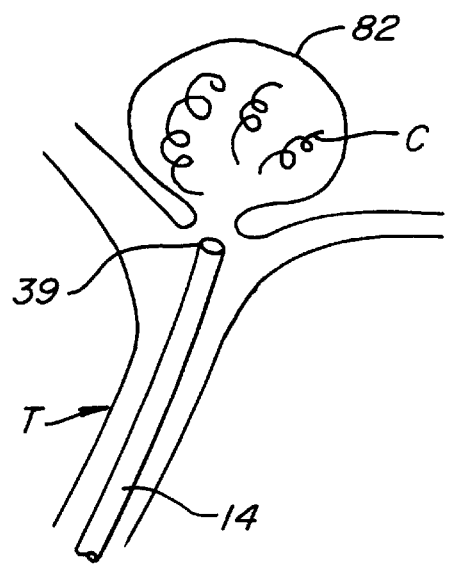

Optionally, as the distal end of the distal body segment 14 approaches the arterial branch B it may become necessary to use the guidewire GW to cause the catheter to enter the target artery T. When the guidewire GW is carried within the distal body segment, as shown in FIG. 12, it is an easy matter to advance the distal tip of the guidewire out of the body segment 14, as shown in FIG. 15. After positioning of the guidewire, the distal body segment 14 may be passed over the guidewire into the target artery T, and the guidewire thereafter withdrawn from the catheter 10. Once in place in the target artery T, the catheter 10 can be used for a variety of therapeutic or diagnostic purposes.

Figure 14:
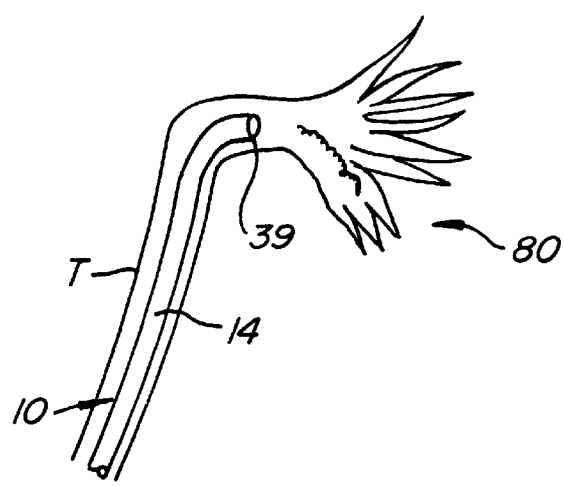
FIGS. 14–16 illustrate use of the flow-directed catheter of the present invention for treatment of an arteriovenous malformation (AVM), an aneurysm, and a tumor, respectively.
Figure 16:
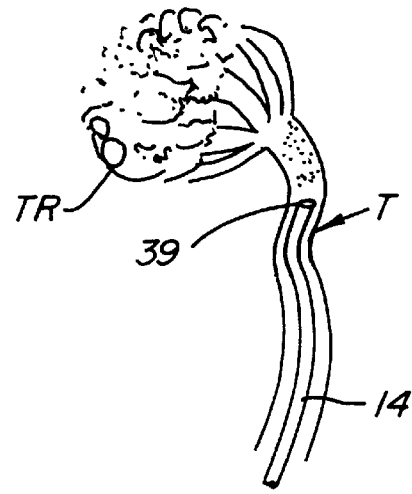

Referring now to FIGS. 14–16, the use of catheter 10 for performing three different therapeutic protocols will be described. FIG. 14, an arterial venous malformation (AVM) 80 is treated by releasing an occluding material, such as a tissue adhesive, embolic particles or embolic coils, from the distal tip 39 to the malformation. In FIG. 15, an aneurysm 82 is treated by the delivery of embolic coils C through the tip 39 of the catheter 10. In FIG. 16, a tumor TR is treated by the release of anti-neoplastic agents through the tip 39 of the catheter. A variety of other conventional therapies can also be carried out using the flow-directed catheters and catheter systems of the present invention.

Although the foregoing invention has been described in some detail by way of illustration and example, for purposes of clarity of understanding, it will be obvious that certain changes and modifications may be practiced within the scope of the appended claims.

What is claimed is:

1. A flow directed catheter comprising:
   a proximal body segment having a proximal end, a distal end, a lumen therethrough, a predetermined flexibility, a predetermined lumen diameter, and a predetermined outside diameter, said proximal segment having substantially constant lumen and outside diameter; and
   a distal body segment having a proximal end joined to the distal end joined to the distal end of the proximal body segment, a distal end, a lumen therethrough, a predetermined flexibility, a predetermined lumen diameter and a predetermined outside diameter said distal segment having substantially constant lumen and outside diameter;
   wherein the flexibility of the distal body segment is substantially greater than that of the proximal segment so that the distal segment is sufficiently flexible to follow blood flow and the proximal section is sufficiently rigid to provide column strength to manipulate the catheter from the proximal end thereof, and wherein an outer surface region of the distal body segment comprises surface irregularities which increase flow resistance between the outer surface region and liquid flow past said region.

2. A flow-directed catheter as in claim 1, wherein the surface irregularities extend over substantially the entire outer surface of the distal body segment.

3. A flow-directed catheter as in claim 1, wherein the surface irregularities comprise at least one of ridges, bumps, cavities, and fibers.

4. A catheter as in claim 1, wherein at least a portion of the body segments includes a radiopaque filler.

5. A catheter as in claim 4, wherein the filler is disposed or concentrated in a pattern.

6. A catheter as in claim 4, wherein the pattern comprises longitudinal stripes.

7. A catheter as in claim 4, wherein the pattern comprises an annular ring.

8. A catheter as in claim 1, wherein the distal body segment is tapered to a smaller diameter in a distal direction.

9. A catheter as in claim 1, wherein at least a portion of the outer surfaces or lumens of the catheter is covered with a hydrophilic material.

10. A flow-directed catheter system comprising:
   (1) a flow-directed catheter including:
      a proximal body segment having a proximal end, a distal end, a lumen therethrough, a predetermined flexibility, a predetermined lumen diameter, and a predetermined outside diameter; and
      a distal body segment having a proximal end joined to the distal end of the proximal body segment, a distal end, a lumen therethrough, a predetermined flexibility, a predetermined lumen diameter and a predetermined outside diameter,
      wherein the flexibility of the distal body segment is substantially greater than that of the proximal segment so that the distal segment is sufficiently flexible to follow blood flow and the proximal section is sufficiently rigid to provide column strength to manipulate the catheter from the proximal end thereof and wherein an outer surface region of the distal body comprises surface irregularities which increase flow resistance between the outer surface region and liquid flow past said region; and
   (2) a sheath having a proximal end, a distal end, and a lumen therethrough, wherein the sheath is slidably disposed over the flow-directed catheter so that the sheath may be axially positioned to selectively enhance the column strength of a proximal portion of the distal body segment.

11. A catheter of claim 1, said catheter comprising:
   a catheter body having a proximal end, a distal end, and a lumen therethrough, wherein the distal end has an inner cylindrical surface at the end of the lumen, an outer cylindrical surface, and an annular end surface, an envelope defined by the inner and outer cylindrical surfaces and the annular end; and
   a radiopaque marker bond disposed near the distal end of the catheter body and recessed with in the envelope.

12. A catheter as in claim 11, wherein the catheter body is composed of an organic polymer and wherein the radiopaque marker is composed of a metal.

13. A catheter as in claim 12, wherein the radiopaque marker is recessed within an annular channel in the inner cylindrical surface.

14. A catheter as in claim 13, wherein a distal end of the radiopaque marker is flush with the annular end surface of the catheter body.

* * * * *